United States Patent
de Oliveira et al.

(10) Patent No.: US 10,896,108 B2
(45) Date of Patent: Jan. 19, 2021

(54) AUTOMATIC FAILURE DETECTION IN MAGNETIC RESONANCE APPARATUSES

(71) Applicant: Siemens Healthcare GmbH, Erlangen (DE)

(72) Inventors: Andre de Oliveira, Uttenreuth (DE); Georg Goertler, Baiersdorf (DE); Atilla Peter Kiraly, San Jose, CA (US)

(73) Assignee: Siemens Healthcare GmbH, Erlangen (DE)

(*) Notice: Subject to any disclaimer, the term of this patent is extended or adjusted under 35 U.S.C. 154(b) by 31 days.

(21) Appl. No.: 16/197,715

(22) Filed: Nov. 21, 2018

(65) Prior Publication Data
US 2019/0155709 A1    May 23, 2019

(30) Foreign Application Priority Data
Nov. 21, 2017  (EP) .................... 17202765

(51) Int. Cl.
*G06F 11/22*   (2006.01)
*G06N 3/08*    (2006.01)
(Continued)

(52) U.S. Cl.
CPC ........ *G06F 11/2263* (2013.01); *G01R 33/543* (2013.01); *G06F 11/3024* (2013.01);
(Continued)

(58) Field of Classification Search
CPC ............... H04L 41/0631; H04L 41/069; H04L 41/0816; H04L 1/00; H04L 43/0823;
(Continued)

(56) References Cited

U.S. PATENT DOCUMENTS 6,751,339 B1 *  6/2004  Windle ................. G06T 11/001
                                                   382/108
7,355,179 B1 *  4/2008  Wood ....................... G06T 1/00
                                                  250/339.11
(Continued)

FOREIGN PATENT DOCUMENTS

EP    1 197 861 A2    4/2002

OTHER PUBLICATIONS

Shi Lei: "Research on fault diagnosis of CT scanner based on probabilistic neural network"; Cyber Technology In Automation, Control And Intelligent Systems (Cyber); 2012 IEEE International Conference On, IEEE; pp. 200-203; (2012).
(Continued)

*Primary Examiner* — Matthew M Kim
*Assistant Examiner* — Matthew N Putaraksa
(74) *Attorney, Agent, or Firm* — Schiff Hardin LLP

(57) ABSTRACT

In a method, a computer and a medical computer for automatic failure analysis in order to provide a cause of failure of the medical imaging apparatus during operation, input data are read into the computer that include raw data or image data, acquired by the imaging apparatus. A set of performance indicators in the input data is calculated by the computer. A trained neural network system is accessed with the calculated performance indicators, in order to provide result data that, in the case of a failure, identify a failure source.

10 Claims, 2 Drawing Sheets

(51) Int. Cl.
*G06N 3/04* (2006.01)
*G01R 33/54* (2006.01)
*G16H 30/20* (2018.01)
*G06F 11/30* (2006.01)
*G06F 11/34* (2006.01)

(52) U.S. Cl.
CPC ....... *G06F 11/3409* (2013.01); *G06N 3/0454* (2013.01); *G06N 3/08* (2013.01); *G06N 3/088* (2013.01); *G16H 30/20* (2018.01)

(58) Field of Classification Search
CPC .... H04L 5/001; H04L 5/0048; G06F 11/2263; G06F 11/3024; G06F 11/3409
See application file for complete search history.

(56) References Cited

U.S. PATENT DOCUMENTS

| | | | |
|---|---|---|---|
| 2004/0205717 A1* | 10/2004 | Chiang | G06F 11/362 717/124 |
| 2005/0063513 A1* | 3/2005 | Hsieh | A61B 6/585 378/98.8 |
| 2005/0157848 A1 | 7/2005 | Miyauchi et al. | |
| 2008/0021994 A1* | 1/2008 | Grelewicz | H04L 43/0805 709/224 |
| 2011/0302461 A1 | 12/2011 | Goertler et al. | |
| 2012/0010495 A1 | 1/2012 | de Oliveira et al. | |
| 2016/0224705 A1* | 8/2016 | Joshi | G06F 30/367 |
| 2017/0169082 A1* | 6/2017 | Bingham | G06F 9/45558 |
| 2018/0098754 A1* | 4/2018 | Li | G01S 15/8927 |
| 2018/0144214 A1* | 5/2018 | Hsieh | G06N 3/08 |
| 2019/0042933 A1* | 2/2019 | Powell | G06N 20/00 |

OTHER PUBLICATIONS

Zhang et al, Text Understanding from Scratch, Technical Report , New York University Computer Science Dept. (2015).
Luc et al, "Semantic Segmentation using Adversarial Networks". arxiv.org/abs/1611.08408 [cs.CV] Nov. 25, 2016.
Badrinarayanan et al. "SegNet: A Deep Convolutional Encoder-Decoder Architecture for Image Segmentation", 5. arXiv:1511.00561v3 [cs.CV] Oct. 10, 2016.
European Search Report dated May 14, 2018, for Application No. 17202765.8.

* cited by examiner

AUTOMATIC FAILURE DETECTION IN MAGNETIC RESONANCE APPARATUSES

BACKGROUND OF THE INVENTION

Field of the Invention

The invention concerns automatic failure analysis and evaluation of machine states in order to provide an identification of the cause of failure of a medical imaging machine, such as a magnetic resonance (MR) scanner, already during operation.

Description of the Prior Art

MR scanners as one type of medical imaging modality are complex systems composed of hundreds of subcomponents, which are very sensitive to environmental changes and must be constantly monitored to guarantee patient and staff safety and high image quality.

Typically, whenever a magnetic resonance system is not working properly, a service engineer is called to resolve the issue. The engineer must evaluate whether the system is working as specified or if there is a system error. To support this evaluation, the service engineer has to make specific assessments and check for proper functionality in order to find the error source. This "manual" approach strongly relies on the experience of the service technician (the know-how to handle a specific situation) and is error prone.

In state of the art, EP 1 197 861 A2 discloses an automatic training unit, which is based on waveform data and which interacts with a knowledge base in order to provide a corresponding system fault of a medical imaging apparatus.

Moreover, it is also the case that, because an MR system is very complex, sometimes users may choose a poor parameterization of measurement protocols that causes image artifacts that mimic system errors. Therefore, for example, poor image quality is not always an error, but may be due to a wrong use of the system, so a differentiation between "wrong application parameterization" and "system error" is required.

SUMMARY OF THE INVENTION

An object of the present invention is to provide a solution for automatic and improved analysis with respect to such system failures. Further, there is a need to provide a failure analysis tool, which improves the sensitivity and/or specificity of failure analysis. Further, the drawbacks of the state of the art systems as mentioned above should be reduced or even overcome.

According to a first aspect of the invention relates to a method for automatic failure analysis (error evaluation) in order to provide a result of the automatic failure analysis, which in case of a failure identifies a cause of the failure of a medical imaging apparatus (e.g. an MR scanner) during operation, has the following steps.

Input data are read into a computer, which may be raw data or image data, acquired by the imaging apparatus in question. The input data may thus be image-related data and metadata, such as text data log files or reference data.

A set of performance indicators (also called key performance indicators) are calculated in the input data by the computer.

A trained neural network is accessed with the calculated performance indicators (or with a change of the calculated performance indicators over time), in order to provide result data, that, in the case of a failure, identify a failure source and, otherwise, identify an operational state of the medical imaging device.

In an embodiment, the result data classify the failure sources with respect to a probability measure. This provides additional information for the user and/or system engineer, helping to evaluate the machine's state or situation. Preferably, a probability for the result is computed. Thus, the result designates the probability measure that indicates the probability that the provided result data are true. For example, a result provided with a low probability has a different impact and meaning for the machine than a result with a high probability (where it makes sense to directly trigger further actions).

In another embodiment, the calculating is executed automatically by extracting the performance indicators directly from the raw data prior to reconstruction of an image. This makes the method and system very efficient and helps to insure safe execution time so that a result may already be provided as soon as possible, and even prior to reconstruction, which is dependent on further resources. Finally, errors may be detected earlier, which may lead to lower costs. In an alternative embodiment, the performance indicators are extracted from the image data, thus during or after image reconstruction.

In another embodiment, calculating is executed automatically by applying a performance measurement algorithm. The performance measurement algorithm transforms information in the raw data (signals) or in the image (reconstructed image) into numeric data, wherein the numeric data represents quality of the acquired image data and/or of the imaging device. Preferably, calculating is executed during reconstruction. For example, an average signal per channel is calculated as performance indicator. Further, a highest relative fast Fourier transformation (in the following abbreviated as FFT) peak may be calculated as performance indicator. Moreover, an average signal to noise ratio may be calculated. In a preferred embodiment of the present invention, all or selected performance indicators are calculated and used for accessing the trained neural network.

An advantage of this feature is that the set of performance indicators may be extended also during runtime of the method and system. Further, the set of performance indicators may be applied differently for each use case, i.e. for each device differently, taking into account the different settings of the machines. Also, it is possible for additional performance indicators to be deduced from the set of performance indicators, originally provided. It is also possible to only consider some performance indicators at a later stage of execution, for example during or after image reconstruction. Thus, the performance indicators need not to be forwarded and input to the trained neural network system at the same time. In another embodiment, a more complex system may be used, to find further performance indicators. For this purpose, another second neural network may be used, which is trained to find further performance indicators based on automatic analysis of existing log files with failure patterns and correlations between error states and machine parameters which may serve as further performance indicators. In alternative embodiments, alternative machine learning methods may be used, like decision trees etc. instead of the second neural network.

In another embodiment, the method further includes observing changes of performance indicators over time. In this case, the trained neural network system is accessed with the observed changes of performance indicators only or in addition to the performance indicators. A change of a performance indicator may indicate a change in the machine's state, which might be a source of a (future) error. This information may be provided in the result data as well and may automatically trigger further data processing (transformations in a normalized form for making the comparable with other machine settings and scenarios) and/or issuance of a warning message.

According to another embodiment, the trained neural network is trained to learn a failure source for a set of performance indicators or changes of performance indicators over time. The neural network has been trained in a prior preparation phase to provide correlations for a machine's state (parametrization of the imaging device) and possible failure sources.

In another embodiment, the input data further include text data (e.g. from log files), stream data, historic data and/or parameter data of the same imaging device or of other (foreign) reference devices. This extends the databases and improves sensitivity of the failure analysis.

According to another embodiment, the trained neural network system is incrementally re-trained based on a detected evaluation of the result data. If, for example, the system provides an incorrect failure source or failure analysis, this could be marked by a user interaction and this information can be fed back into the system again for later incremental re-training.

According to another embodiment, image performance indicators include the average signal per channel, the highest relative FFT peak, and/or the average SNR.

The invention also encompasses a computer in the form of an automatic failure analyzer, for use with a medical imaging device. The automatic failure analyzer has an input interface, adapted to read input data, including raw data or image data, acquired by the imaging device, a calculation processor configured to calculate a set of performance indicators in the input data, a trained neural network system, which may be stored in a memory and which provides a correlation between performance indicators and possible failure sources or failure states, and an output interface, which provides result data for the operation of the medical imaging device.

The analyzer may also have a result evaluation processor configured to receive an evaluation signal from the user in order to evaluate the computed result retrospectively with respect to truth and quality, indicating whether or not and to what degree the computed failure source was the real cause of failure. This evaluation signal is fed back to the neural network system to re-train the same in order to improve quality.

In another aspect the invention refers to a medical imaging device with such an automatic failure analyzer as mentioned above.

In the following a short definition of terms is given.

The invention relates to an automatic failure analysis, which comprises an error evaluation, if any and an evaluation of the system state or the state of the imaging device. For example, the failure analysis may provide the result, indicating that up to now, no failure exists but in the near future a failure may be expected, e.g. due to an over-utilization of specific resources.

Input data mainly refer to image related data and may comprise raw data before image reconstruction. It also possible to apply the method to already reconstructed images, which are typically stored in the machine or device locally in an archive. Besides image-related data (raw data signals and reconstructed images), other data, also in different formats are considered for failure analysis. In particular, text data from log files from earlier scans, stream data from key performance indicators of historic scans, pre-reconstruction data, comprising alignment and adjustment data or additional information from earlier reconstructions, external images, which have been acquired on other scanner devices but may be used for calculation of performance indicators as well as scanner settings and parameterized features are to be considered. All these factors may be used for calculation of performance indicators and may be fed into the fully connected layers of the artificial neural network.

In the preferred embodiment, the imaging apparatus is an MR apparatus or scanner with a number of subcomponents. Other embodiments can be computed tomography systems and ultrasound systems.

The performance indicators are usually defined in a training or preparation phase and serve as a quality measure for the generated images. The performance indicators, thus, indicate performance of the imaging apparatus. They may also indicate a proper functionality of the same.

Calculating refers to an automatic computation which have as input the images or the raw data signals and have as output at least one performance indicator, which typically is represented in a digital format or as number values. Preferably, at least three different performance indicators are generated.

The (artificial) neural network (in the following abbreviated as ANN) system is trained in a training phase. The input layer receives the calculated performance indicators (or a change of the calculated performance indicators over time). The one or more hidden layer(s) is/are adapted to process the data and to apply an activation function and forward that data to the output layer. The output layer serves to provide result data. The ANN may comprise multiple convolutional and pooling layers. The ANN may be a deep learning network with multiple hidden layers.

In a more complex embodiment, the neural network system may be deployed as ANN framework with several ANNs, wherein each input (raw/image data, text data, historical data, scanner settings etc.) is processed by an appropriate deep neural network to prepare features from the data. Quantized text and stream data can be similarly processed. Parameter data can be directly processed by the fully connected layers where the final classification occurs. The system as a whole can be trained end-to-end using stochastic gradient decent with a softmax cross entropy loss function. Cross entropy can be used to define the loss function in machine learning and optimization. The cross entropy loss is ubiquitous in modern deep neural networks and in statistical learning theory. The softmax function is often used in the final layer of a neural network-based classifier. Such networks are commonly trained under a log loss (or cross-entropy). Features for each dataset will be automatically computed during training. Generative Adversarial Networks (GAN) can be employed to classify the correct assertion probability in comparison to those made by an expert if available. This can be used to train the network to achieve better performance. Once trained and deployed the system can monitor itself and report any issues without the need for an on-site technician. Since the probability of each outcome is computed, low probabilities in all discrete classes can be binned into an unknown error class and require standard on-site service. The probabilities reported can be used by the technician as a hint to what is the issue. In either cases, the system can suggest which parts are needed for the service to allow for better preparedness and logistics for failure processing and troubleshooting. If the system provides a wrong result or makes an incorrect recommendation, this can be marked and the input data along with the correct classification can be marked for later incremental or re-training. Additional states of evaluation or input data can be easily added to the framework but would require retraining. Also, duplications of the network can be used in a cascaded fashion where, for example, the first network identifies a coil issue while the second can focus on specific types of coil issues.

In a preferred embodiment, the data and parameters of the result can be provided in an anonymized fashion to improve security of the system.

The result is a dataset in a digital format. It may comprise different sections. In case of a failure, the result comprises a failure source or an indication of the same. The result helps identifying the failure source or may be the failure source as such, like e.g. "failure in coil xyz". The result may also comprise a probability measure, for example: "Source: Coil defect with 90% probability". If no failure is detected, the result may represent a state of the device and may indicate future failures or other future states (including a state of proper and correct operation without any failures) which are expected with a calculated probability. The result may also be used as quality assurance test, providing that the device or components thereof is/are not broken. The result may also be an indication to check for special component performance according to the factory specifications.

The result may also provide a trend for expected future device operation, based on the detected performance indicators. The trends could be further processed automatically to identify cross-correlations to possible problems and failures.

According to a preferred embodiment, the result is provided locally on the imaging apparatus. Further, the result may be transmitted to other computing entities, like a server, which may aggregate result data from multiple different devices in order to remotely obtain cross-correlations and to apply statistical evaluations.

The present invention also encompasses a non-transitory, computer-readable data storage medium that is encoded with programming instructions (program code) that, when the storage medium is loaded into a computer or a computer system of an imaging apparatus, cause the computer or computer system to operate the imaging apparatus so as to implement any or all embodiments of the method according to the invention, as described above.

DESCRIPTION OF THE PREFERRED EMBODIMENTS

Figure 1:
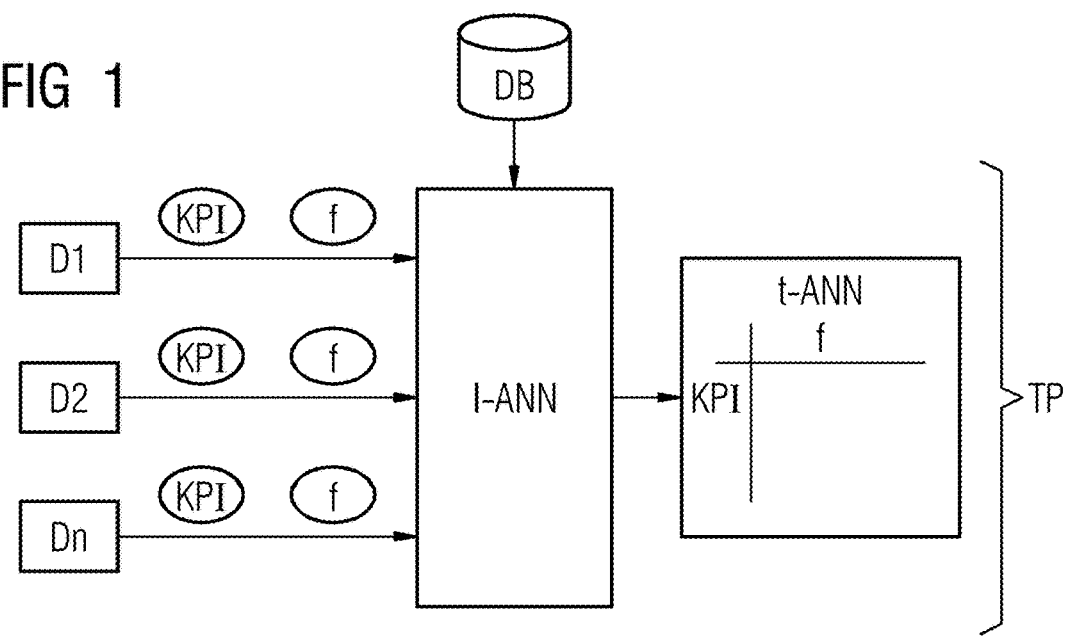
FIG. 1 is a schematic illustration of a system for automatic failure analysis in a training phase in an overview.

FIG. 1 shows an overview of a system 1 for automatic analysis of an operating state of a medical imaging device, like an MR device D. The analysis includes automatic failure or error diagnosis without any human interaction (of a service technician). In case of a failure, the cause and source of the detected failure should be identified automatically by the system, based on learned data of a trained artificial neural network (ANN). The method may be executed during operation of the MR scanner, and even during the scans.

The method may be executed directly on the imaging device D or on a separate computing entity.

In a training phase, the neural network 1-ANN is trained with training data from a plurality of devices D1, D2, Dn in order to generate a trained neural network t-ANN. During operation of the devices D, (key) performance indicators KPI are detected and are fed into an input layer of the network. In addition, and at a later stage, failures f may also be provided to the neural network to be trained 1-ANN. The network 1-ANN may further be provided with additional data from a database DB, for example with log files, historical data and metadata. In this training phase TP the neural network is trained in order to provide a correlation or cross-correlation between performance indicators KPI and failures f. Typically, a set of performance indicators is correlated or cross-correlated with a set of failures or a failure pattern. The neural network may be a convolutional network, processing on two functions to produce a third function, which is typically viewed as a modified version of one of the original functions.

Figure 2:
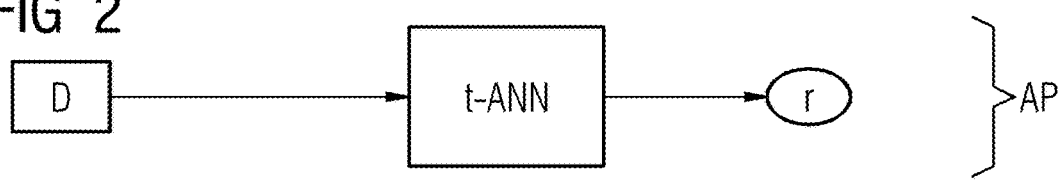
FIG. 2 is a schematic illustration of a system in an application phase according to a preferred embodiment of the invention.

The so trained neural network t-ANN may be applied in an application phase AP for the method according to the invention. The trained network t-ANN may be provided with "real" operational data of the MR scanner D for applying the learned information in order to provide a result r. The result r may indicate possible failures causes and sources in case a failure is detected. This is schematically shown in FIG. 2.

Figure 3:
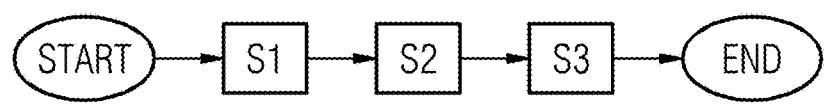
FIG. 3 is a flowchart of a method according to a preferred embodiment of the invention.

With respect to FIG. 3 a typical workflow of the method according to a preferred embodiment of the present invention is shown. Aber Start of the method, input data are read in in step S1. Input may refer to raw data of the imaging device D and/or to completely or partially reconstructed images, both acquired by the imaging device D. In step S2, a set of performance indicators KPI in the input data is calculated. Preferably, an average signal per channel, a highest relative FFT peak and an average signal to noise ratio is calculated as performance indicator set KPI. In step S3 the result dataset r is computed by accessing the trained neural network system t-ANN with the calculated performance indicators KPI of step S2. The result r comprises an indication of a possible failure source in case of a failure otherwise the device's state and operation is provided.

Figure 4:
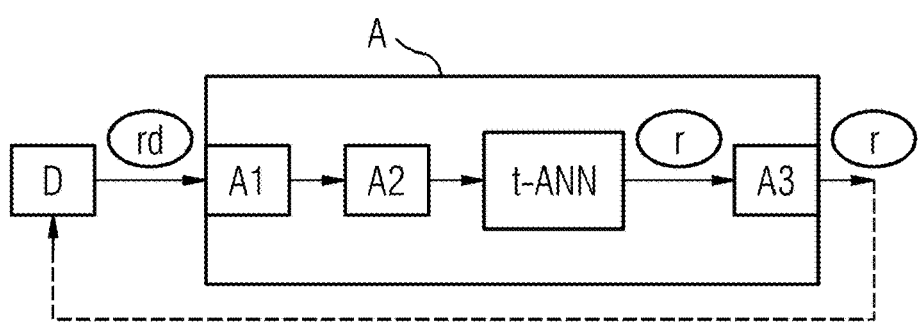
FIG. 4 shows a first embodiment of a system with components of a neural network in schematic representation.

FIG. 4 shows an analyzer A for automatic failure analysis support with its subcomponents according to a first embodiment in more detail. Each of the devices D interacts with the analyzer A. The analyzer A may be provided as separate computing entity, as shown in FIG. 4, but may also be directly integrated into the device D itself. In this first embodiment, the analyzer A is operated with raw data rd, which are fed into the input layer of the trained neural network t-ANN. For this purpose, the analyzer A comprises an input interface A1, which is adapted for reading input data, and in this embodiment raw data rd, acquired by the imaging device D.

The analyzer A further has a calculation processor A2 configured to calculate a set of performance indicators KPI in the raw data rd. The set of calculated performance indicators KPI is forwarded into the trained neural network system t-ANN, wherein the trained neural network system t-ANN provides a correlation between performance indicators KPI and possible failure sources as mentioned above. An output interface A3 is adapted for providing the computed result data r for the operational state of the medical imaging device D. In case of a failure, possible failure sources are indicated. The result r may be output on a user interface of the medical device D (not shown) or may be fed back to the system optionally together with an evaluation of the quality of the provided result, i.e. of a user's indication on how good the failure source has been identified.

Figure 5:
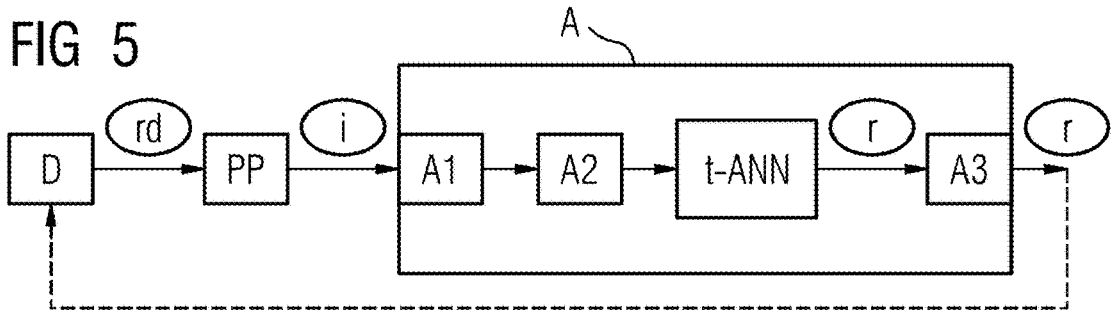
FIG. 5 shows a second embodiment of a system with components of a neural network also in a schematic representation.

A second embodiment is shown in FIG. 5. Here, the analyzer A is operated on the basis of image data. As can be seen, the raw data rd from the device D are forwarded into a reconstruction unit and/or post processing unit PP for reconstructing the image i. The reconstructed image i is then fed into the input layer of the trained neural network t-ANN via the input interface A1. Then the method continues as in the first embodiment, described in detail above with respect to FIG. 4.

Both embodiments shown in FIGS. 4 and 5 provide the analyzer A for executing the method for automatic failure analysis on a separate entity than the device D itself. In these embodiments, of course, the analyzer A and the device D are interconnected for data exchange via a network. However, it is also possible, to implement the analyzer A directly into the device D according to several technical embodiments. According to a first embodiment, the analyzer A is implemented on each of the devices D which need to be verified and error checked. According to a second embodiment, the analyzer A is only implemented on dedicated devices D, which serve the other devices D with respect to failure analysis. This has the advantage that only those devices D may be selected for the additional analyzing functionality, which have sufficient technical resources, i.e. with respect to processing power, bandwidth and/or memory capacity etc.

The invention has several advantages. With the automatic failure analysis, errors may be reduced. Further, severe system errors may be distinguished from simple errors or even failures in parametrization (applicational errors). Further, analysis may be improved with respect to precision. Manual measurements and quality assessments can be quantified. Moreover, the valuable time of a service engineer may be shifted to the severe cases so that productivity of the medical system as well as throughput and turn-around per engineer may be increased.

The specificity and sensitivity in the detection, handling and prediction of system failures is increased. As a consequence, service costs are reduced, since less visits will be needed to fix an error (traveling costs), less non-broken parts will be exchanged, and less time will be needed (salaries). The invention provides an intrinsic anonymization of the image relevant information which has been up to now one of the main impediments in using the image data. The calculation of image performance indicators KPI can be performed quickly during image reconstruction and/or acquisition without the need for any additional hardware. The information could be used to predict system failures thus supporting customers in the planning/reduction of system down time. The information could be used to support image application improvements and to support automatic image quality improvements. The system is able to automatically adapt to new input data types and sources along with new failure modes.

In general, the invention relates to use a trained deep convolutional neural network t-ANN combined with image related key performance indicators KPI and track the KPIs over time (for example: average image SNR over time) to support error detection and providing suggestions for correction. Additionally, a selection of performance indicators KPIs is used, namely those KPIs which may curate image data and support the automatic clustering and classification of image quality related sources (application/parametrization error or system error). Finally, it is proposed to use the image KPIs to support the correction of wrongly parameterized imaging protocols.

In another preferred embodiment, a convolution neural network t-ANN with three fully connected layers is used to classify images i with respect to possible failure classes (e.g. no error, coil element failure, coil failing, component failing, a more detailed quality analysis should be performed, wrong MR parameterization, unknown error). A similar network can be used to classify or analyze raw MR data rd. Upon training, features (or performance indicators KPI) optimal to the task will be automatically created. Multi-dimensional data can be used (1D, 2D, 3D, etc.). The convolutional layers must be appropriate to the input data. Given a large enough receptive field, parameters such as total average can be computed as an internal parameter for classification.

In the following it will be described how image key performance indicators KPI may curate image data and indicate possible failures.

In MRI, the image raw data rd contain much more information than the final reconstructed image. For example: during reconstruction coil channel data is combined to form images, or during acquisition calibration measurements are used to enable parallel imaging reconstruction methods such as GRAPPA or SENSE.

Certain performance indicators KPI could easily be extracted from the raw data rd during the reconstruction. In the following examples of correlations between performance indicators KPI and system failures f are shown, which serve as a basis to train the neural network 1-ANN.

Average signal per channel $$Av\_Signal_c = \sum_{x=1}^{xtot} \sum_{y=1}^{ytot} Signal_C(x, y),$$

where xtot, ytot are the total number of pixels in the x or y direction of the acquired signal rd for a given 2D image. In some circumstances it is expected that if the average signal is close to 0, there is likely a problem with a given coil element. This information alone could be used to distinguish, for example, image errors resulting from "wave like pattern" which could either be caused by spikes or bad image parameterization or failures in coils.

Figure 6:
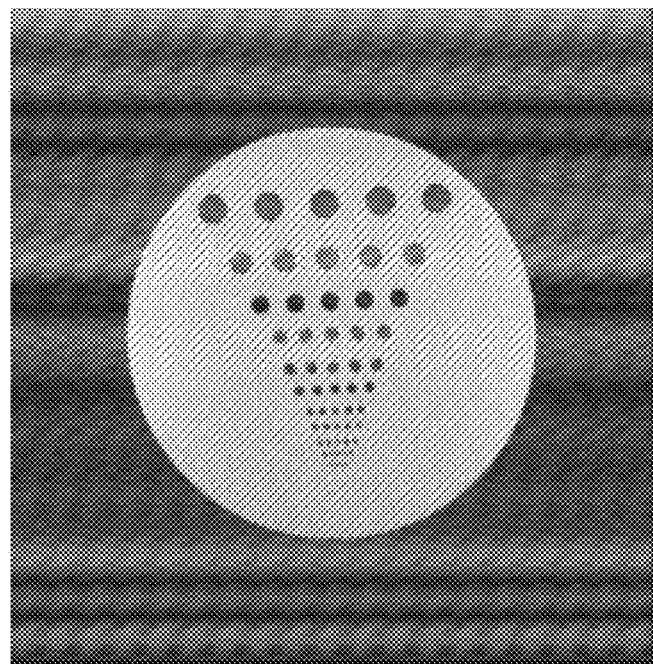
FIG. 6 shows an example of a wave-like pattern extracted from an image.

FIG. 6 shows an example of wave like pattern artifact extracted from an MR image.

Highest Relative FFT Peak $$\text{Highest relative } FFT \text{ peak} = \max \frac{(FFT\ (kx,\ ky)}{FFT\ (0,\ 0)}$$

The relative FFT peak could be an indication of spikes, which could be easily calculated by each generated image i. If this performance indicator KPI is higher than a pre-defined value (sequence dependent, coil dependent), than there is a probability of presence of spikes.

Since the detection of spikes is very difficult as it might depend on very specific conditions (sequence usage etc.), having this information could considerably reduce the time needed to identify the failure source.

Figure 7:
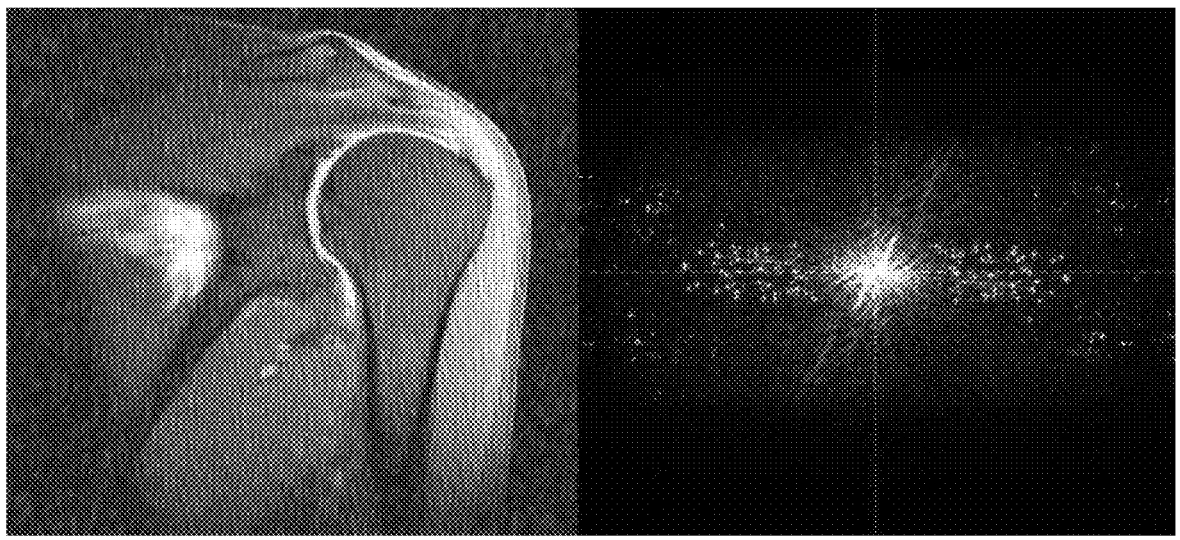
FIG. 7 shows an example of spikes in image space and k-space extracted from an image.

FIG. 7 shows an example of spikes in image space and k-space extracted form MR image.

Average Signal to Noise Ratio (SNR)

Generally, performance indicators KPI may be extracted from images which could be used for error detection. Moreover, it is possible to automatically compute performance indicators KPI from images i, based on deep learning networks designed to find optimal features as performance indicators to correlate to failures f.

Further, information contained in images could significantly increase the sensitivity of the log files based systems (e.g. XMART).

The table below shows examples of possible correlations, which are learned by the trained neural network t-ANN.

| KPI | Could positively correlate with which failures? | Could negatively correlate with which failures? |
| --- | --- | --- |
| Average signal per channel | If too low -> coil element failure | Metal artifact, too high iPAT factor selection, spikes |
| Highest relative FFT peak | If too high -> spikes | |
| Average SNR for the same protocol | If too low -> possibly quality analysis must be performed, frequency is shifting | |
| Average SNR for the same coil | If too low -> possibly quality analysis must be performed, coil is failing | |
| Average SNR for the same system | If too low -> together with other KPI could indicate that a component is about to fail | |

Automatic calculation of SNR could be a challenge since it requires the identification of a region of interest where the signal is present and where the signal is not present. To overcome this issue, the following features are provided, for example:

a. Just create a region of interest in the middle of the image with fixed dimensions. Since in most cases, the observed object is in the isocenter, it is very likely that the ROI will be positioned at the object.

b. Use automatic segmentation algorithms such as AutoAlign. Just position the ROI at the position of a detected landmark or even create an ROI using landmarks (such as in abdomen dot engine care bolus).

c. Similar to a, a ROI at the edge of an image could represent a region of noise.

d. Similar to b, a landmark "not part of body" could be used to define regions outside of the body.

Regardless of the method, which is applied the following equation is to be applied:

Average SNR=(Average signal at noise ROI)/(Average signal at object ROI)

The average SNR for a given image, series of images, coil, system, could provide a reliable parameter to observe the change of performance over time and possibly even replace quality analysis measurements needs. Since there are so many parameters that could influence SNR, sequences with fixed parameters such as the AutoAlign scout may be used.

In addition to the above approaches using these manually defined features or indicators, deep-learning approaches allow for automated generation of unique features that are optimized for the classification task at hand. The raw data can be fed into a multi-layer convolutional network that is trained and internally generates features as described above.

In the following it will be described how to use performance indicators KPI to extract (further) data relevant for error detection in MR systems.

The term "iPAT" refers to a parallel imaging implementation. It stands for integrated parallel imaging techniques and is the general term for the entire family of receiver coil-based data acceleration methods. When using parallel imaging methods, spatial information is partly acquired from the receive-field of the RF coil elements, and partly from k-space (i.e. gradient) encoding. By comparison, with conventional, non-parallel imaging we only use k-space encoding. Using iPAT means that it is possible to acquire fewer gradient echoes and so acquire less data per volume during an EPI time series. The iPAT number refers to the image acceleration factor—or in the case of EPI, the reduction in the length of the echo train. For example, with iPAT=2 half of the number of echoes for EPI as without iPAT, while with iPAT=4 only one quarter of the gradient-encoded data are acquired than would be needed without iPAT. There are two types of iPAT available for nearly all sequences on the scanner: GRAPPA ("generalized autocalibrating partially parallel acquisitions") which is k-space-domain based, and mSENSE ("modified sensitivity encoding") which is image-space based. GRAPPA is recommended by Siemens on its scanners and has been shown to be better than mSENSE for fMRI. Generally, it is possible to decide of how much acceleration you want to have, such as a factor of 2, 3, or 4. iPAT=1 means iPAT is turned off.

While the current invention has been described in relation to its preferred embodiments, it is to be understood that this description is for illustrative purposes only. For example, the device D may be a medical CT apparatus or another technical apparatus, for image acquisition. For the person skilled in the art it is clear that the invention may also be used for other performance indicators KPI as well. Accordingly, it is intended that the invention be limited only by the scope of the claims appended hereto.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for automatic failure analysis of a medical imaging apparatus during operation of the medical imaging apparatus, comprising:

reading in input data, comprising raw data or image data, acquired by the medical imaging apparatus into a computer; in said computer, calculating a set of performance indicators in the input data, the set of performance indicators comprising: an average signal per channel of said medical imaging apparatus, a highest relative Fast Fourier Transform (FF1) peak, and an average signal-to-noise ratio (SNR);

from said computer, accessing a trained neural network system with said calculated performance indicators in order to use said trained neural network system to produce result data such that, if a failure of said medical imaging apparatus exists, a cause of said failure of said medical imaging apparatus is identified, and otherwise an operational state of the medical imaging apparatus is identified; and from said computer, presenting said result data at a display screen.

2. A method as claimed in claim 1 comprising, in said computer, organizing said result data for display at said display screen so as to classify multiple possible failure causes of the medical imaging apparatus with respect to a probability measure of each of said multiple failure causes.

3. A method as claimed in claim 1 comprising calculating said performance indicators in said computer by automatically directly extracting said performance indicators from raw data in said image data, before reconstruction of image data.

4. A method as claimed in claim 1 comprising calculating said performance indicators in said computer by automatically executing a performance measurement algorithm that operates on said input data.

5. A method as claimed in claim 1 further comprising:

in said computer, detecting changes of said performance indicators over time; and accessing said trained neural network system with said detected changes of said performance indicators.

6. A method as claimed in claim 1 comprising training said neural network so as to learn a cause of failure of the medical imaging apparatus for a set of performance indicators or changes in said performance indicators over time.

7. A method as claimed in claim 1 comprising reading into said computer, with said input data, data selected from the group consisting of text data, stream data, historic data, and parameter data.

8. A method as claimed in claim 1 comprising incrementally retraining said trained neural network based on an evaluation of said result data.

9. An automatic failure analyzer for use with a medical imaging apparatus, the automatic failure analyzer comprising:

an input interface configured to read in input data, comprising raw data or image data, acquired by the medical imaging apparatus;

one or more processors configured to calculate a set of performance indicators in the input data, the set of performance indicators comprising an average signal per channel of said medical imaging apparatus, a highest relative Fast Fourier Transform (FF1') peak, and an average signal-to-noise ratio (SNR);

a trained neural network system configured to produce result data as a correlation between performance indicators and causes of failure of said medical imaging apparatus; and an output interface configured to present said result data at a display screen.

10. The medical imaging apparatus of claim 9, further comprising:

a storage device configured to store at least one of the trained neural network system and a second trained neural network, wherein the second trained neural network is configured to learn further sets of performance indicators.

* * * * *